US00PP37765P2

(12) United States Plant Patent
Hofmann

(10) Patent No.: US PP37,765 P2
(45) Date of Patent: Oct. 13, 2026

(54) ***MANDEVILLA* PLANT NAMED 'INMAN 528'**

(50) Latin Name: *Mandevilla sanderi*
Varietal Denomination: INMAN 528

(71) Applicant: INNOVAPLANT ZIERPFLANZEN GmbH & Co. KG, Gensingen (DE)

(72) Inventor: Birgit Hofmann, Rudesheim am Rhein (DE)

(73) Assignee: INNOVAPLANT ZIERPFLANZEN GmbH & Co. KG, Gensingen (DE)

( * ) Notice: Subject to any disclaimer, the term of this patent is extended or adjusted under 35 U.S.C. 154(b) by 0 days.

(21) Appl. No.: 19/546,386

(22) Filed: Feb. 22, 2026

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Mandevilla* plant named 'INMAN 528', characterized by its broadly upright plant habit; moderately vigorous growth habit and moderate growth rate; freely branching habit; dense and bushy appearance; medium green-colored leaves; early, freely and continuous flowering habit; and medium-sized star-shaped light and dark purplish pink-colored flowers with dark yellow-colored throats.

2 Drawing Sheets

Figure 1:
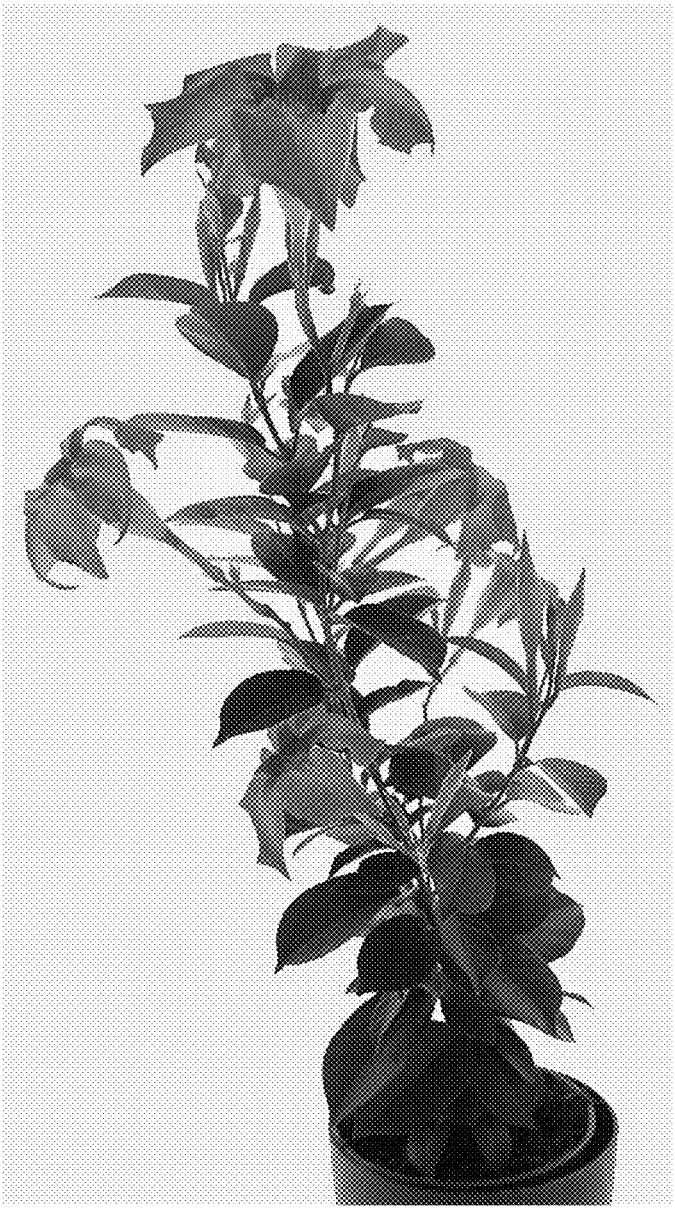

Botanical designation: *Mandevilla sanderi.*
Cultivar denomination: 'INMAN 528'.

CROSS-REFERENCED TO CLOSELY-RELATED APPLICATIONS

A European Community Plant Breeder's Rights application for the instant plant was filed by the Applicant/Assignee of the instant application, Innovaplant Zierpflanzen GmbH & Co. KG of Gensingen, Germany on Aug. 4, 2025, application number 2025/1741, and published on Oct. 15, 2025. Foreign priority is not claimed to this European Community Plant Breeder's Rights application.

BACKGROUND OF THE INVENTION

The present invention relates to a new and distinct cultivar of *Mandevilla* plant, botanically known as *Mandevilla sanderi* and hereinafter referred to by the name 'INMAN 528'.

The new *Mandevilla* plant is a product of a planned breeding program conducted by the Inventor in Johannesburg, South Africa and Heidesheim, Germany. The objective of the breeding program is to create new freely branching *Mandevilla* plants that flower early and freely and have attractive flowers that resist fading and sunscalding.

The new *Mandevilla* plant originated from a cross-pollination conducted by the Inventor in Johannesburg, South Africa in January, 2020 of a proprietary breeding selection of *Mandevilla sanderi* identified as code number d17-4129-21, not patented, as the female, or seed parent with a proprietary breeding selection of *Mandevilla sanderi* identified as code number d17-4129-24, not patented, as the male, or pollen, parent. The new *Mandevilla* plant was discovered and selected by the Inventor as a single flowering plant from within the progeny of the stated cross-pollination in a controlled greenhouse environment in Heidesheim, Germany in June, 2022.

Asexual reproduction of the new *Mandevilla* plant by vegetative cuttings in a controlled greenhouse environment in Heidesheim, Germany since July, 2022 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INMAN 528'. These characteristics in combination distinguish 'INMAN 528' as a new and distinct *Mandevilla* plant:

1. Broadly upright plant habit.
2. Moderately vigorous growth habit and moderate growth rate.
3. Freely branching habit; dense and bushy appearance.
4. Medium green-colored leaves.
5. Early, freely and continuous flowering habit.
6. Medium-sized star-shaped light and dark purplish pink-colored flowers with dark yellow-colored throats.

Plants of the new *Mandevilla* can be compared to plants of the female parent selection. Plants of the new *Mandevilla* differ primarily from plants of the female parent selection in the following characteristics:

1. Plants of the new *Mandevilla* are more vigorous than plants of the female parent selection.

2. Leaves of plants of the new *Mandevilla* are lighter green in color than leaves of plants of the female parent selection.
3. Flowers of plants of the new *Mandevilla* are larger than flowers of plants of the female parent selection.

Plants of the new *Mandevilla* can be compared to plants of the male parent selection. Plants of the new *Mandevilla* differ primarily from plants of the male parent selection in the following characteristics:

1. Plants of the new *Mandevilla* are more vigorous than plants of the male parent selection.
2. Plants of the new *Mandevilla* are more freely branching and denser than plants of the male parent selection.
3. Leaves of plants of the new *Mandevilla* are lighter green in color than leaves of plants of the male parent selection.
4. Flower petals of plants of the new *Mandevilla* are flatter than flower petals of plants of the male parent selection.
5. Flowers of plants of the new *Mandevilla* are smaller than flowers of plants of the male parent selection.

Plants of the new *Mandevilla* can also be compared to plants of *Mandevilla sanderi* 'Inmanbepiwhe', not patented. In side-by-side comparisons, plants of the new *Mandevilla* differ primarily from plants of 'Inmanbepiwhe' in the following characteristics:

1. Plants of the new *Mandevilla* are more vigorous than and not as compact as plants of 'Inmanbepiwhe'.
2. Plants of the new *Mandevilla* are more freely branching and denser than plants of 'Inmanbepiwhe'.
3. Leaves of plants of the new *Mandevilla* are lighter green in color than leaves of plants of 'Inmanbepiwhe'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'INMAN 528' grown in a container.

Figure 2:
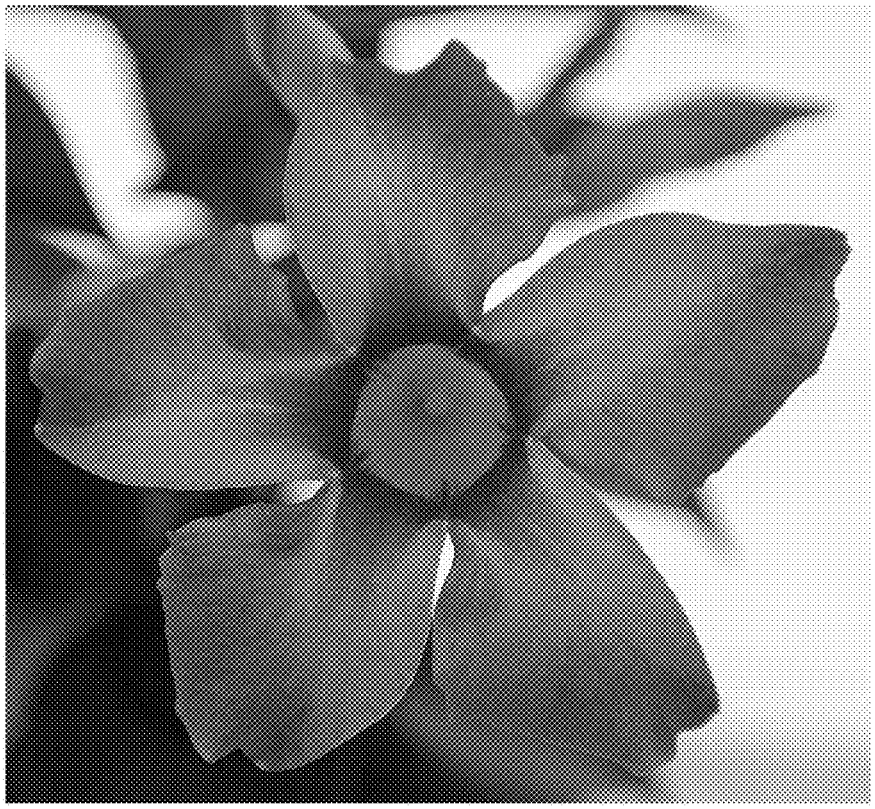

The photograph on the second sheet (FIG. 2) is a close-up view of a typical flower of 'INMAN 528'.

DETAILED BOTANICAL DESCRIPTION

The aforementioned photographs and following observations, measurements and values describe plants grown during the summer in 12-cm containers in a glass-covered greenhouse in Heidesheim, Germany and under cultural practices typical of commercial *Mandevilla* production. During the production of the plants, day temperatures ranged from 12° C. to 35° C. and night temperatures ranged from 12° C. to 18° C. Plants were pinched one time and were four months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'INMAN 528'.

Parentage:

*Female, or seed, parent*.—Proprietary breeding selection of *Mandevilla sanderi* identified as code number d17-4129-21, not patented.

*Male, or pollen, parent*.—Proprietary breeding selection of *Mandevilla sanderi* identified as code number d17-4129-24, not patented.

Propagation:

*Type*.—By vegetative cuttings.

*Time to initiate roots, summer*.—About three weeks at temperatures ranging from 20° C. to 35° C.

*Time to initiate roots, winter*.—About three weeks at temperatures ranging from 20° C. to 25° C.

*Time to produce a rooted young plant, summer*.—About 20 to 25 days at temperatures ranging from 20° C. to 35° C.

*Time to produce a rooted young plant, winter*.—About 25 to 30 days at temperatures ranging from 20° C. to 25° C.

*Root description*.—Thick, fleshy; typically white in color, actual color of the roots is dependent on substrate composition, water quality, fertilizers, substrate temperature and physiological age of roots.

*Rooting habit*.—Low branching; medium density.

Plant description:

*Plant and growth habit*.—Broadly upright plant habit; roughly broadly obovate in overall shape; moderately vigorous growth habit and moderate growth rate; and freely branching habit; dense and bushy appearance.

*Plant height, soil level to top of foliar plane*.—About 40.5 cm.

*Plant height, soil level to top of floral plane*.—About 42.8 cm.

*Plant diameter* (*spread*).—About 22.8 cm.

*Lateral branch description*.—Branching habit: Freely branching habit, typically about five secondary lateral branches per primary lateral branch; pinching enhances lateral branch development. Length: About 18.4 cm. Diameter: About 3 mm. Internode length: About 2.9 cm. Aspect: About 30° to 40° from main branch axis. Strength: Strong. Texture and luster: Smooth, glabrous; slightly glossy; becoming woody with development. Color, developing: Close to 144A. Color, developed: Close to 143C; when woody, close to N199B and N199C.

Leaf description:

*Arrangement*.—Opposite, simple.

*Length*.—About 6.4 cm.

*Width*.—About 3.8 cm.

*Shape*.—Broadly elliptic to obovate-elliptic.

*Apex*.—Apiculate to short aristate.

*Base*.—Truncate.

*Margin*.—Entire; not lobed.

*Texture and luster, upper and lower surfaces*.—Smooth, glabrous; slightly coriaceous; moderately glossy.

*Venation pattern*.—Pinnate.

*Color*.—Developing leaves, upper surface: Close to 143A. Developing leaves, lower surface: Close to 146A and 146B. Fully developed leaves, upper surface: Close to a blend of NN137A and 139A; venation, close to 143B. Fully developed leaves, lower surface: Close to a blend of 146A and 146B; venation, close to 145B.

*Petioles*.—Length: About 7 mm. Diameter: About 2 mm by 2 mm. Strength: Moderately strong. Texture and luster, upper and lower surfaces: Smooth, glabrous; slightly to moderately glossy. Color, upper surface: Close to 143B. Color, lower surface: Close to 150B and 150C.

Flower description:

*Flower type and flowering habit*.—Single star-shaped salverform flowers arranged in terminal and axillary cymes; flowers face outwardly to slanting upright; freely flowering habit with about seven flowers per inflorescence and about 45 flower buds and open flowers developing per plant.

*Natural flowering season*.—Plants flower continuously from spring into the autumn in Germany; plants begin flowering about 10 to 14 weeks after propagation depending on environmental and cultural conditions.

*Flower longevity*.—Individual flowers last about two weeks on the plant; flowers not persistent.

*Fragrance*.—None detected.

*Inflorescence height*.—About 12.2 cm.

*Inflorescence diameter*.—About 12.8 cm.

*Flower buds*.—Length: About 5.4 cm. Diameter: About 8 mm. Shape: Narrowly oblanceolate. Texture and luster: Smooth, glabrous; slightly glossy. Color: Close to 37B; proximally, close to 144C; distally, close to 145B slightly tinged with close to 37C.

*Flowers*.—Appearance: Flared trumpet, corolla fused and five-parted. Diameter: About 8.2 cm by 8.2 cm. Depth (length): About 6.5 cm. Throat diameter: About 1.2 cm. Tube length: About 5.5 cm. Tube diameter: Proximally, about 4 mm; distally, about 1.6 cm.

*Corolla*.—Quantity and arrangement: Five petals arranged in a single whorl; lower portion of the petals are fused into a funnelform tube. Petal length, tube and free lobes: About 9.3 cm. Petal length, free lobes: About 3.8 cm. Petal width, free lobes: About 2.6 cm. Petal shape and appearance: Unequal and broadly spatulate. Petal apex: Apiculate, unequal. Petal margin: Entire; moderately undulate. Petal texture and luster, upper surface: Smooth, glabrous; velvety; matte. Petal texture and luster, lower surface: Smooth, glabrous; slightly velvety; slightly glossy. Throat texture: Smooth, glabrous; velvety. Tube texture: Smooth, glabrous; slightly velvety. Color: Petal, when opening, upper surface: Close to 61C and 63C. Petal, when opening, lower surface: Close to 58B and 62A. Petal, fully opened, upper surface: Close to N66B, 62A and 62B; venation, similar to lamina colors; color does not fade with subsequent development. Petal, fully opened, lower surface: Close to 61C; main vein, close to NN155B and lateral venation, close to 61C; color does not fade with subsequent development. Throat: Distally, close to a blend of N57B and 58B; proximally, close to 15A and toward the base, close to N144B; venation, similar to lamina colors. Tube: Close to 145C tinged with close to 55B; towards the base, close to N144B; at the base, slightly tinged with close to 173C; venation, similar to lamina colors.

*Sepals*.—Quantity and arrangement: Five sepals arranged in a single whorl. Calyx length: About 9 mm. Calyx diameter: About 6 mm. Length: About 9 mm. Width: About 1.5 mm. Shape: Lanceolate. Apex: Narrowly acuminate. Base: Broadly cuneate and fused at the base. Margin: Entire. Texture and luster, upper surface: Smooth, glabrous; slightly glossy. Texture and luster, lower surface: Smooth, glabrous; matte. Color: When developing, upper and lower surfaces: Close to 145B to 145C; at the apex, close to 145A. Fully developed, upper and lower surfaces: Close to 145C; at the apex, close to 145A.

*Peduncles*.—Length: About 6.7 cm. Diameter: About 2 mm. Strength: Strong. Aspect: About 27.5° from lateral branch axis. Texture and luster: Smooth, glabrous; moderately glossy. Color: Close to 143B.

*Pedicels*.—Length: About 1.5 cm. Diameter: About 2 mm. Strength: Strong. Aspect: About 30° from peduncle axis. Texture and luster: Smooth, glabrous; moderately glossy. Color: Close to 143C.

*Reproductive organs*.—Stamens: Quantity and arrangement: Typically five; basifixed; anthers connivent. Filament length: About 2 mm. Filament color: Close to 151D. Anther shape: Narrowly oblong. Anther size: About 1.25 mm by 9 mm. Anther color: Close to 162C. Pollen amount: None observed. Pistils: Quantity: Typically one. Pistil length: About 2.2 cm. Style length: About 2 cm. Style color: Close to 145C. Stigma diameter: About 2 mm. Stigma shape: Club-shaped. Stigma color: Close to 148D. Ovary color: Close to 144B.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 5° C. to about 40° C. and to be suitable for USDA Hardiness Zones 9 to 13.

It is claimed:

1. A new and distinct *Mandevilla* plant named 'INMAN 528' as herein illustrated and described.

* * * * *